(12) United States Patent
Adahan

(10) Patent No.: US 7,503,910 B2
(45) Date of Patent: Mar. 17, 2009

(54) SUCTIONING SYSTEM, METHOD AND KIT

(76) Inventor: Carmeli Adahan, 11 Netivei Am, Ramot, Jerusalem 97552 (IL)

( * ) Notice: Subject to any disclaimer, the term of this patent is extended or adjusted under 35 U.S.C. 154(b) by 0 days.

(21) Appl. No.: 11/344,007

(22) Filed: Feb. 1, 2006

(65) Prior Publication Data

US 2007/0179460 A1    Aug. 2, 2007

(51) Int. Cl.
*A61M 35/00*    (2006.01)

(52) U.S. Cl. .......... 604/319; 604/40; 604/313; 604/543

(58) Field of Classification Search ........ 604/319, 604/40, 313, 543
See application file for complete search history.

(56) References Cited

U.S. PATENT DOCUMENTS

| | | | |
|---|---|---|---|
| 3,416,461 A | 12/1968 | McFarland | |
| 4,634,430 A | 1/1987 | Polaschegg | |
| 4,661,093 A | 4/1987 | Beck et al. | |
| 4,739,791 A | 4/1988 | Adahan | |
| 4,930,997 A | 6/1990 | Bennett | |
| 5,370,610 A * | 12/1994 | Reynolds | 604/43 |
| 5,419,687 A | 5/1995 | Adahan | |
| 5,599,333 A | 2/1997 | Atkinson | |
| 5,636,643 A * | 6/1997 | Argenta et al. | 128/897 |
| 5,645,081 A | 7/1997 | Argenta et al. | |
| 5,662,599 A * | 9/1997 | Reich et al. | 602/79 |
| 5,776,119 A | 7/1998 | Bilbo et al. | |
| 6,042,560 A | 3/2000 | Niederberger | |
| 6,071,267 A | 6/2000 | Zamierowski | |
| 6,471,982 B1 * | 10/2002 | Lydon et al. | 424/443 |
| 6,648,862 B2 | 11/2003 | Watson | |
| 7,128,735 B2 * | 10/2006 | Weston | 604/543 |
| 2001/0029956 A1 | 10/2001 | Argenta et al. | |
| 2002/0151826 A1 | 10/2002 | Ramey et al. | |
| 2003/0014022 A1 | 1/2003 | Lockwood et al. | |
| 2003/0040687 A1 | 2/2003 | Boynton et al. | |
| 2003/0050594 A1 | 3/2003 | Zamierowski | |
| 2003/0097100 A1 | 5/2003 | Watson | |
| 2004/0039243 A1 | 2/2004 | Bearnson et al. | |
| 2004/0059284 A1 | 3/2004 | Nash et al. | |
| 2004/0064132 A1 | 4/2004 | Boehringer et al. | |
| 2004/0199840 A1 | 10/2004 | Takeoka et al. | |
| 2005/0004534 A1 | 1/2005 | Lockwood et al. | |
| 2005/0192548 A1 | 9/2005 | Dolliver et al. | |

FOREIGN PATENT DOCUMENTS

| | | |
|---|---|---|
| DE | 24 01 643 A1 | 7/1975 |
| DE | 102 15 896 A1 | 10/2003 |
| EP | 0 156 211 A2 | 10/1985 |
| EP | 0 865 304 B1 | 9/1998 |
| GB | 2 378 734 A | 2/2003 |

(Continued)

*Primary Examiner*—Tatyana Zalukaeva
*Assistant Examiner*—Ilya Y Treyger
(74) *Attorney, Agent, or Firm*—The Nath Law Group; Jerald L. Meyer; Jiaxiao Zhang

(57) ABSTRACT

A suction head in fluid communication with a pump head provides a sub-ambient working pressure to a medical site, enabling drainage thereof to a waste container and/or enhancing healing at the site. A passive pressure regulator enables the working pressure to be maintained at a desired level independent of the fluid flow through the system.

26 Claims, 3 Drawing Sheets

FOREIGN PATENT DOCUMENTS

| | | |
|---|---|---|
| WO | 96/05873 A1 | 2/1996 |
| WO | 97/18007 A1 | 5/1997 |
| WO | 00/02016 A1 | 1/2000 |
| WO | 03/016719 A1 | 2/2003 |
| WO | 03/030966 A1 | 4/2003 |
| WO | 03/057070 A2 | 7/2003 |

* cited by examiner

SUCTIONING SYSTEM, METHOD AND KIT

FIELD OF THE INVENTION

This invention relates to medical suctioning systems and methods, and more specifically to such systems and methods that apply negative pressure to physiological areas and the like.

BACKGROUND OF THE INVENTION

There are many medical situations in which applying suctioning to an area of the body may be beneficial, for example: applying a negative pressure to a wound or burn and /or draining the same, draining the trachea, draining fluids from organs and other parts of the body being operated on or being treated, including treatments of a dental nature. A number of systems and methods have been developed for providing medical suctioning.

In WO96/05873 an apparatus is disclosed having a porous foamed pad connected by a tube to a canister. A vacuum pump is located within a housing having a recess for receiving the canister. A bacterial filter positioned over the outlet of the canister, and a vacuum pump sucks wound drainage fluids into the canister.

In WO 97/18007 a portable wound treatment apparatus is disclosed, including a housing containing a suction pump and a canister for containing fluids drawn from the wound. The housing is supported on a harness or belt worn by the patient and is connected to a porous dressing at the wound site by a catheter.

In WO 03/016719, a vacuum pump is disclosed having a drive and a disengageable pumping system connected thereto, and a two- or three-chambered canister within which solids, liquids and gases may be separated from one another.

In U.S. Pat. No. 6,648,862 the vacuum desiccator low pressure vacuum pump and trap and is transportable upon a user's person. The device includes a desiccator cartridge containing a fluid trapping agent, and the desiccator cartridge is connected to a vacuum pump member for providing a low vacuum pressure to the interior chamber of the desiccator cartridge. A single passage, one-way, gas/liquid flow pathway connects the inlet port of the desiccator cartridge to an occlusive dressing covering the wound to be drained. A control circuit includes one or more ancillary circuits for controlling operation of the device, such as: a power circuit, a moisture sensor, a timer circuit, a vacuum pressure sensor, and a pressure differential sensor.

In U.S. Pat. No. 5,645,081, a method and apparatus are disclosed, in which a negative pressure is applied to a wound sufficient in time and magnitude intended to promote tissue migration and facilitate closure of the wound.

In GB 2,307,180 (EP 0865304), a porous dressing is applied on a wound from which fluid is drawn into a canister via a catheter using portable suction pump. The pump is contained in housing and is worn on a harness or belt. Overfilling of canister is prevented by a filter contained in the canister and a pressure sensor which detects pressure reductions in tube between canister and pump which occur when drainage liquid covers the filter. A filter is placed between pump and canister, and pressure at the wound site is monitored by a conduit connected to the porous dressing.

In U.S. Pat. No. 4,739,791 a fluid collection container is disclosed, having an inlet connectable to a fluid source and an outlet connectable to a suction source. The container contains a closure member that closes the outlet port when the container is full. The closure member is integrated with a vent valve that is mounted to the container near the outlet.

In WO 03/030966, a system is disclosed for treating a patient with a wound, and comprises a bandage, a receptacle, and a vacuum source. The bandage comprises a cover to seal about the wound and to define a space above the wound in which a vacuum is to be formed. The bandage further comprises a port providing communication with the space. The receptacle is connected to the port to receive exudate from the wound and is provided to be placed below the wound. The vacuum source is spaced apart from the receptacle, is connected to the receptacle.

In WO 03/057070, a ventilated bandage system is disclosed for use with a wound. The system includes a bandage positioned adjacent to the wound to create a sealed environment around the wound. A vacuum source of the system is in communication with the bandage to create negative pressure between the bandage and the wound. The system may also include a first passageway or vent in communication with the bandage and with the surrounding atmosphere, and a second passageway in communication with the bandage and with the vacuum source.

In US 2005/192548, a wound drainage system is disclosed for draining fluid from a wound of a patient. The system includes a drain catheter, and a suction means applies suction at the drain catheter such that fluid is drawn from the wound. While drawing fluid from the wound, a controller periodically increases and decreases in an active manner the application of suction at the drain catheter.

SUMMARY OF THE INVENTION

The present invention relates to a vacuum system (or apparatus) for providing a sub-ambient pressure to a medical target volume, and thus enables fluids to be drained from such a target volume. Accordingly, the invention also includes a corresponding system for draining fluids from such a target volume.

Herein, the terms "medical target volume" or "target volume" relate to any part of the body of a human or animal, external or internal, regarding which it is desired to apply a sub-ambient pressure to and/or to drain fluids therefrom. By way of non-limiting example, such a target volume may comprise a wound/burn, the trachea, the stomach, intestines, any body cavity (including for example the intra-oral cavity, sinuses, etc.), an organ or other part of the body being operated on or regarding which there is bleeding or regarding which it is beneficial to remove fluids therefrom.

The system of the invention comprises:

a suction head having an inlet arrangement adapted for being in fluid communication with said target volume;

a vacuum pump in fluid communication with said suction head, said vacuum pump being adapted for providing a working pressure in said system below external ambient pressure;

a waste container defining a collection volume for collection of materials that may be drained from said target volume in fluid communication with at least one of said vacuum pump and said inlet arrangement; and a passive pressure regulation system for passively regulating said working pressure, said passive pressure regulation system being in fluid communication with said suction head upstream of the said waste container.

The suction head may be of any shape, size or form without limitation, typically suitable to the particular target volume that is being suctioned. For example, for external body applications in which the target volume is associated with wounds, burns and the like, the suction head may comprises an enclosure sealable to a perimeter of the wound/burn so as to define a confined volume comprising said target volume. In internal body applications, for example tracheal drainage and the like, the suction head may comprise a drain catheter or other similar arrangement having at least one lumen in fluid communication with said pump, and said inlet arrangement comprises at least one aperture adapted for providing fluid communication between said target volume and said at least one lumen.

As will become clearer herein, by "passive" in relation to the pressure regulation system is meant that the pressure regulation system is configured for responding, and un fact responds, directly to a change in parameters such as the pressure drop across the pressure regulation system, and is driven directly by the change in parameter, to open or close, in contrast with so-called active pressure regulation systems in which operation thereof is actively controlled by a controller that is of itself substantially unmoved by the changes in the parameters, such as for example an electronic controller or computer, according to preset instructions. Such an active pressure regulation system functions with the aid of a powered drive mechanism that selectively opens or closes the regulation system responsive to instructions or signals provided by the controller, and the controller may provide instructions to open/close at periodic intervals, for example. Thus, the passive pressure regulation system of the present invention is substantially unpowered and/or uncontrolled by an external control unit, and rather operates to open or close solely by virtue of the pressure difference across the pressure regulation system being within or exceeding a predetermined threshold, which may optionally be set within a variable range.

In described embodiments, the pressure regulation system comprises a venting valve arrangement adapted for enabling ingress of external ambient air into the system responsive to a reduction in said working pressure below a predetermined datum pressure with respect to said external ambient pressure and for discontinuing said ingress when said datum pressure is restored. The venting valve arrangement may comprise an inlet port having a valve seat and in fluid communication with said ambient air, an outlet port in fluid communication with said vacuum system, and a valve seal biased for sealingly closing with respect to said valve seat by means of a resilient element generating a biasing force of magnitude substantially less than and in a direction generally opposed to a pressure-induced force acting on said valve seal when said working pressure is less than said datum pressure.

Optionally, the venting valve arrangement comprises an adjustment mechanism for adjusting said datum pressure. In one form of the valve arrangement, this comprises an inlet port in fluid communication with said ambient air and an outlet port in fluid communication with said vacuum system, and a valve seal biased for sealingly closing said inlet port by means of a resilient element generating a biasing force of magnitude substantially less than and in a direction generally opposed to a pressure-induced force acting on said valve seal when said working pressure is less than said datum pressure, and wherein said adjustment mechanism comprises a bias adjusting arrangement for adjusting the magnitude of said biasing force. The resilient element may comprise a compression spring mounted in a suitable housing such as to urge said valve seal towards said valve seat, and said bias adjusting arrangement comprises a compression control mechanism for adjusting the compression of said spring.

The pressure regulation system may be connected to the suction head permitting selective fluid communication between said target volume and said external ambient air, enabling ingress of external ambient air into said target volume responsive to a reduction in said working pressure below a predetermined datum pressure and discontinuing said ingress when said datum pressure is restored.

In any case, the pressure regulation system may be mounted in a location upstream or distal of the waste container, and may further be located as close as possible to the target volume, proximate to, i.e. just downstream or proximal, or comprised at the suction head. In some embodiments, the pressure regulation system may also be located upstream or distal of the suction head, for example when the suction head comprises a wound enclosure. By the mounting location is meant either the location where the pressure regulation valve is actually located, or, where the pressure regulation system comprises a dedicated conduit downstream thereof to transmit the pressure of the pressure regulation valve to a particular location of the vacuum system, where such a conduit is actually connected to the vacuum system. By "proximate" is meant that the pressure regulation system may closer to the suction head than to the waste container in terms of fluid flow paths between the three components.

Thus, the passive pressure regulation system is in fluid communication with said suction head upstream of the said waste container.

Herein the terms "upstream" and "downstream" are in relation to the general flow direction from the target area (or into the target area) towards the pump head, and beyond. Similarly, the terms "distal" and "proximal" are in relation to the general flow direction from the target area (or into the target area) to the pump head, and beyond.

The pressure regulation system may be connected to said suction head directly or via a suitable conduit. In some embodiments, the pressure regulation system may be in selective fluid communication with an outlet port of said vacuum pump and said external ambient air such as to allow ingress of at least one of fluid from said vacuum pump outlet port and said external ambient air when said working pressure is below said datum pressure.

The passive pressure regulation system of the invention thus operates in direct response to a particular change in pressure at or close to the suction head, and relieves pressure thereat when the vacuum level drops to below a pre-set level, regardless of the actual volume flow rate of the air ingress through the pressure regulation system, and thus operates to maintain substantially constant the operating pressure in the vacuum system responding almost instantaneously to any departure from the set working pressure.

A feature of such a passive pressure regulation system is that it may be manufactured in a relatively cheap manner compared with active pressure regulation systems, and thus may be integrally formed or connected with other disposable elements of the system, for example, the waste container.

The vacuum pump may comprise a pump head that is releasably operatively coupled to a pump drive unit, wherein said pump head is fixed to or integral with said waste container.

In particular, the pump head and pump drive unit are adapted for enabling quick, easy and simple manual connection and disconnection of the two components, without the need for tools. Thus the pump head and the pump drive unit are attachable and detachable one with respect to the other.

The pump head comprises a pump chamber and a reciprocable pump member that defines part of the pump chamber, and the pump chamber is adapted to expand and contract by two-way forced reciprocation of the pump member under the action of a drive element in the form of a reciprocating member comprised in the pump drive unit. The pump head and the pump drive unit are constructed so that attaching the pump head to the pump drive unit brings the reciprocating pump member and the drive element (reciprocating member) to a position that provides, during operation of the pump drive unit, for their engagement and for reciprocation of the pump member by means of the driving element.

The pump drive unit may comprise first attachment means, and said pump head and/or container may comprise second attachment means, the two attachment means allowing said attaching of the pump head to the pump drive unit by a simple manipulation without tools. Further, the pump head and pump drive unit may be constructed so that said first and second attachment means provide detachment of said drive unit from said pump unit by a manipulation including at the most manual unfastening without tools and one detaching motion, and the same detaching motion disengages said reciprocal pump member from said driving element.

The pump head may comprise a pump inlet port and a pump outlet port, and the pump member may be in the form of a suitable deformable diaphragm arrangement, reciprocable by means of said pump drive unit, to induce said working pressure in said vacuum system. At the same time, the drive unit may comprise a reciprocation drive for driving a reciprocating member, and said diaphragm is releasably engageable with said reciprocating member responsive said pump head being coupled to said pump unit. The reciprocating member and the diaphragm may be conformally shaped such that when coupled one with the other a vacuum is created therebetween as air is expelled, and the vacuum maintains the two components coupled, until a user actively decouples the reciprocating member and the diaphragm one from the other, typically automatically as the pump head is disconnected from the pump drive unity. For example one of the reciprocating member and the diaphragm may comprise a suction cup arrangement for engagement with respect to a substantially smooth surface of the other one of the reciprocating member and the diaphragm. The reciprocating member may be in the form of a reciprocating head having a second diaphragm, or, in the form of a piston head arrangement, for example. Other arrangements enabling automatic engagement between the pump head and pump unit may also be provided.

A part of the pump head may be accommodated in the waste container, wherein the pump diaphragm is facing a direction generally away from said collection volume, and wherein said pump inlet port and a pump outlet port are at least partially within said collection volume. In one embodiment, the pump inlet port is in fluid communication with said suction head via a conduit that passes through the wall of the container, said pump outlet port is in fluid communication with said collection volume and wherein said waste container is vented to said external ambient air.

In another embodiment, the pump inlet port is in fluid communication with said suction head via said collection volume, and said pump outlet port is vented to said external ambient air. In such an embodiment, the pressure regulation system may be operatively connected to said suction head via a suitable first conduit and wherein said pressure regulation system is in selective fluid communication with said pump outlet port and said external ambient air such as to allow ingress of at least one of fluid from said vacuum pump outlet port and external ambient air into said target volume responsive to a reduction in said working pressure below a predetermined datum pressure and such as to discontinue said ingress when said datum pressure is restored. Further, the waste container may be in fluid communication with said suction head via a suitable second conduit, and optionally the first conduit and the second conduit may be in fluid communication one with another.

At least some, and preferably all of the pump head, waste container, suction head and pressure regulation system are configured for being disposable.

Optionally, the pump head and waste container are reversibly lockably engaged with said pump drive unit by means of a latch arrangement.

The present invention also refers to a kit for use with the system of the invention, in particular comprising all the elements of the system other than the pump drive unit. These elements may be disposable, having a relatively low economic cost compared with the economic cost of the pump drive unit for example, or with the economic cost associated with cleaning, sterilizing and recycling such components. Thus, such a kit may comprise:

a vacuum pump head adapted for releasable operative connection to a pump drive unit, said pump head comprising a pump inlet and a pump outlet for enabling working fluid to be pumped through the pump during operation thereof;

a waste container defining a collection volume for collection of drained materials in fluid communication with at least one of said vacuum pump head;

wherein said vacuum pump head is one of attached to or integral with said waste container such that at least one of said pump inlet and said pump outlet is accommodated in said collection volume.

Such a kit may thus also comprise a suction head and/or a passive pressure regulation system as disclosed herein.

In one particular form, the kit comprises:

a suction head having an inlet arrangement adapted for being in fluid communication with said target volume;

a pump head adapted for being releasably operatively connected to a pump drive unit, said pump head comprising a pump inlet port, a pump outlet port and a suitable deformable diaphragm arrangement adapted for reciprocable operation by means of said pump drive unit when connected thereto;

a waste container defining a collection volume for collection of drained materials from said target volume, wherein said pump head is one of fixed to or integral with said waste container such that said pump inlet port and said pump outlet port are accommodated in said collection volume, wherein said pump inlet port is in fluid communication with said suction head via a conduit connecting said pump inlet port with said suction head, at least a portion of said conduit being accommodated in said collection volume, wherein said pump outlet port is adapted for discharging into said collection volume, and wherein said waste container is vented to external ambient air; and a venting valve arrangement mounted to one of said conduit and suction head adapted for enabling ingress of external ambient air into the system responsive to a reduction in said working pressure below a predetermined datum pressure with respect to said external ambient pressure, such as to induce suction flow of materials from said target volume when in use, and for discontinuing said ingress when said datum pressure is restored.

In another form, the kit comprises:

a suction head having an inlet arrangement adapted for being in fluid communication with said target volume;

a pump head adapted for being releasably operatively connected to a pump drive unit, said pump head comprising a pump inlet port, a pump outlet port and a suitable deformable diaphragm arrangement adapted for reciprocable operation by means of said pump drive unit when connected thereto;

a waste container defining a collection volume for collection of drained materials, wherein said pump head is fixed to said waste container such that said pump inlet port and said pump outlet port are accommodated in said collection volume, wherein said pump inlet port is in fluid communication with said suction head via said collection volume, and said waste container is in fluid communication with said suction head via a first conduit, and wherein said pump outlet port is vented to external ambient air; and a venting valve arrangement in fluid communication with said target volume via a second conduit, said valve arrangement being mounted to said waste container and in selective fluid communication with said pump outlet port for enabling ingress of at least one of fluid from said vacuum pump outlet port and external ambient air into the system responsive to a reduction in said working pressure below a predetermined datum pressure with respect to said external ambient pressure, such as to induce suction flow of materials from said target volume, and for discontinuing said ingress when said datum pressure is restored.

Optionally, the said diaphragm comprises a suction cup arrangement for engagement with said pump drive unit.

The present invention also relates to a vacuum system comprising all the elements of a kit as disclosed herein and a pump drive unit, wherein the vacuum pump is in fluid communication with said suction head, the vacuum pump being adapted for providing a working pressure in said system below external ambient pressure, said vacuum pump comprising said pump head releasably operatively connected to said pump drive unit, wherein said pump head comprises a pump inlet port, a pump outlet port and a suitable deformable diaphragm arrangement reciprocable by means of said pump drive unit to induce said working pressure in said vacuum system;

The present invention is also directed to a method for providing a sub-ambient pressure to a medical target volume or for draining fluids therefrom, comprising:

(a) inducing a working pressure in said target volume below external ambient pressure;

(b) providing a collection volume for collection of drained materials from said target volume; and (c) regulating the working pressure in said target volume to provide a positive pressure gradient between said target volume and said collection volume such as to aid flow of said materials from said target volume to said collection volume.

Optionally, step (c) comprises allowing ingress of external ambient air at or near to the target volume responsive to a reduction in said working pressure below a predetermined datum pressure with respect to said external ambient pressure and discontinuing said ingress when said datum pressure is restored. Further optionally, the method may comprise allowing recirculation of fluid, in particular air, between said collection volume and said target volume together with said ingress of external ambient air.

Thus, according to the invention, a suction head in fluid communication with a pump head provides a sub-ambient working pressure to a medical site, enabling drainage thereof to a waste container and/or enhancing healing at the site. A passive pressure regulator enables the working pressure to be maintained at a desired level independent of the fluid flow through the system.

According to the invention, the waste container and pump may be connected in any serial order with respect to the wound enclosure, for example with the waste container may be distally or proximally located (in terms of the fluid flow path from the suction head) from the wound enclosure with respect to the pump.

Some features of the invention include the following. The adjustable pressure regulator or relief valve may be integrated with the wound enclosure or in fluid connection therewith via a tube or conduit, such that the vacuum conditions or negative or sub-ambient pressure applied at the wound may be accurately controlled thereby, in a passive manner, irrespective of the pump flow or exudates flowing from the wound in the direction of the pump. When the negative pressure is controlled at one end of a tube within which exudates are being moved by the force of such negative pressure, a pressure differential is created across the exudates, which moves it. This pressure differential alters the regulator set pressure. In the present invention, the regulator pressure may be transferred directly to the wound by way of a conduit substantially free of exudates, thus controlling the negative pressure at the point of suction, accurately.

When the sub-ambient pressure reaches the set level of the pressure regulator, the regulator opens to introduce airflow in the general direction of the wound so as to maintain the pre-set sub-ambient pressure level. The flow of air from the pressure regulator towards the general direction of the wound substantially prevents exudates or other fluids from the wound from entering the pressure regulator, or where appropriate, the tube or conduit between the regulator and the wound. The flow of air through the pressure regulator is generally continuous and enables the system to operate at a set vacuum pressure independent of the actual air flow, and renders the wound enclosure vented or non-airtight, as distinguishable from conventional non-vented wound closures, as well as from wound enclosures that are vented by means of a vent opening, which renders the vacuum conditions dependent on the flow through the vent.

The pump flow can be low at all negative pressure settings of the regulator (also referred to herein as a relief valve), since the set negative pressure of the regulator is obtained almost instantaneously as soon as the regulator opens to ambient, regardless of the actual flow, providing for low pump flow, low energy consumption as well as substantially silent or low-noise (acoustic) operation. The described method of controlling the negative pressure at a location distant from the pump which generates such negative pressure may be employed for various applications, such as medical suctioning, In most medical applications, it may be desired to maintain suctioning within predetermined limits to avoid tissue damage that may occur at high suctioning.

According to another aspect of the present invention, there is provided a waste collection canister or container, integral with the negative pressure regulating valve, whereby the air entering the relief valve is the air pumped to generate the negative pressure, thus circulation of the pump flow in a closed loop prevents the contaminated pumped air from being discharged to the atmosphere, as is common with other negative pressure systems.

According to a further aspect of the present invention, there is provided a vacuum system for practicing the above method. The vacuum system may use a totally disposable vacuum pump, whereby the pump is integrated into the waste canister, such that attaching the pump to its drive will simultaneously attach the waste canister. The integration of the pump into the waste canister eliminates any conduit between the pump and the waste canister, providing for ease of disposability, as well as reducing the noise level generated by the pump which is separated from its surrounding by the waste canister, doubling as a sound barrier.

According to another aspect of the present invention, there is provided a disposable pump with a diaphragm which has a suction cup formed on its outer surface, for the purpose of engaging the pump to its drive by having a suction cup coupling when the drive contacts the diaphragm suction cup.

Another feature of the invention is that the pump drive unit operates the vacuum pump in a reciprocating manner that may induce flow or pressure pulsations to the wound area, which in turn may enhance wound drainage. This pulsation effect may be obtained in embodiments where the pump inlet is connected directly to the wound enclosure, rather than via a waste canister.

Another feature of the invention is that the selective venting effect provided by the pressure regulator serves to vent the wound enclosure when the pressure therein has dropped below a threshold level, allowing relative quick movement of exudate entering the conduit from the enclosure, and into the waste collection container before the exudates dries or coagulates and occludes the tube.

Another feature of the invention is that the integral unit, comprising the pump head and waste container, optionally together with the wound enclosure and conduit(s) may be easily disconnected from the pump drive unit and disposed of after use, providing an alternative economical and medical solution to that of decontaminating pump parts of the prior art.

Yet another feature of the invention is that it can provide a generally reduced operating noise level as compared with the operation of prior art devices. For example, in the embodiments described herein, the pump head is accommodated within the waste container, which dampens any noise generated by the pump drive unit. Moreover, in embodiments where the waste container is in fluid communication with the wound enclosure via the pump head, only a small volume of air needs to be removed from the wound enclosure to achieve the required vacuum conditions. In such embodiments, the pump may operate at relatively low power ratings, required for relatively low flow rates, which has a corresponding low noise benefit.

A feature particularly of the second embodiment is that by having the pressure regulator housed within a sleeve in the waste container, it is possible to recycle the pumped air from the wound back into the system via the regulator, reducing the possibility of exhausting contaminated air back into the environment, and also facilitates the disposal of the waste container and disposable peripherals such as the tubing, regulator and wound enclosure.

BRIEF DESCRIPTION OF THE DRAWINGS

In order to understand the invention and to see how it may be carried out in practice, a number of embodiments will now be described, by way of non-limiting example only, with reference to the accompanying drawings, in which.

DETAILED DESCRIPTION OF EMBODIMENTS

Figure 1:
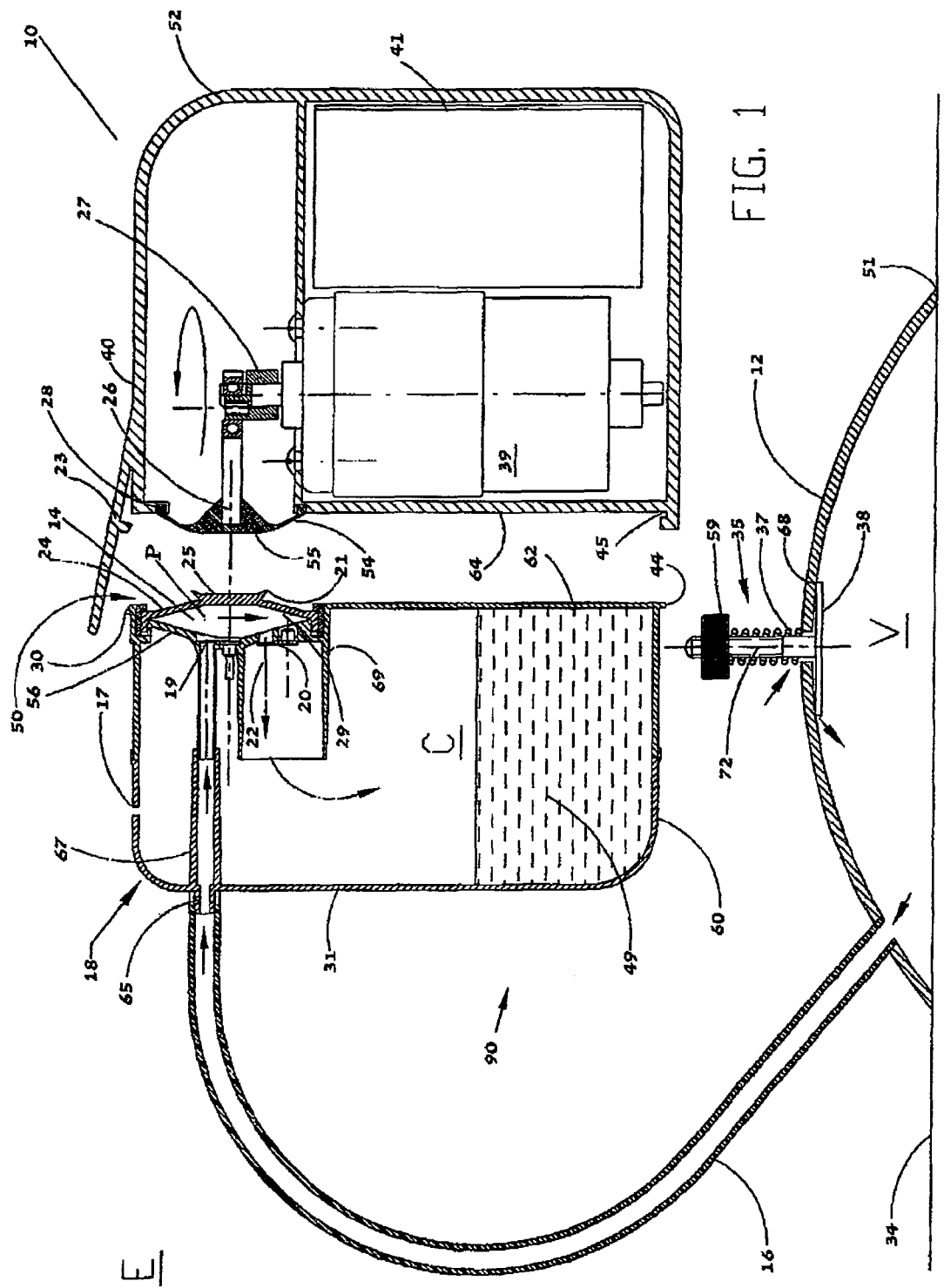
FIG. 1 is a schematic illustration in cross-sectional side view of a first embodiment of the invention, wherein the pump-head/container unit is detached from the pump drive unit, and the wound enclosure is fixed to a wound site.

A vacuum system for providing, i.e. applying, a sub-ambient pressure to a medical target volume, and thus for enabling fluids to be drained therefrom according to a first embodiment of the present invention, illustrated in FIG. 1 and generally designated with the numeral 10, comprises a suction head, a vacuum pump 50, waste canister or container 31, and pressure regulator 35.

The suction head has an inlet arrangement adapted for being in fluid communication with the target volume, and is in the form of wound enclosure 12, which is associated with the target volume comprising a wound, for example. The enclosure 12 has an outer perimeter 51 that is sealable to the periphery of the wound area on the body 34. The enclosure 12 defines a confined volume V including the target volume over the exposed parts of the wound from which it is desired to remove under suction liquids and other flowable materials, which may include biological or non-biological materials, though at times it may be desired merely to maintain a negative pressure in the confined volume V over the wound to promote healing thereof.

In other embodiments, the suction head may instead comprise, for example, a drain catheter or the like, for applying a predetermined vacuum to a medical target area, such as for example the intra-oral cavity, trachea, an organ of the body being operated on, and so on. Such a drain catheter may comprise at least one lumen in fluid communication with the pump 50, and the inlet arrangement may comprise at least one aperture adapted for providing fluid communication between the target volume and the at least one lumen.

The pump 50 comprises a pump head 14 that is releasably coupled to a pump drive unit 40 for operation therewith. The drive unit 40 comprises a housing 52 accommodating a powered drive, such as an electric motor 39, and a battery pack 41 for powering the motor. Additionally or alternatively, the motor 39 may be provided with power form an external source, such as for example an electric mains (not shown). A reciprocating mechanism 27, comprising a crank and a reciprocating head 26 coupled to a rod, is provided within the housing 52 for converting the rotary drive of the motor 39 to reciprocating motion for reciprocating head 26. The reciprocating head 26 comprises a flexible membrane 54 having a periphery 28 thereof suitably sealingly anchored to a frame in said housing 52, such that a relatively smooth surface 55 of the membrane 54 is exposed with respect to the housing 52, and such as to prevent contamination of the inside of the housing 52.

The pump head 14 comprises a pump inlet port 19 and a pump outlet port 20 comprised on a substantially rigid part 56 of the pump head 14, and a flexible diaphragm 24 that is connected at its periphery to the periphery of the rigid part 56 to define a pump working chamber 29 having a variable pump volume P. Suitable one-way valves are provided at the pump inlet port 19 and a pump outlet port 20 to ensure fluid flow in one direction through the pump head 14 from inlet port 19 to outlet port 20. The flexible diaphragm 24 is deformable from a first position in close proximity to the rigid part 56 defining a minimum pump volume P, and a second position (when maximally spaced from the rigid part 56 during operation of the system) defining a maximum pump volume P. An outer-facing side of the diaphragm 24 comprises a suction cup 25, integrally or otherwise joined thereto, adapted for releasbly engaging with respect to said smooth surface 55. Optionally, and as illustrated in FIG. 1, the suction cup 25 may comprise a peripheral lip 21.

The waste container 31 comprises a suitable housing 60 defining a collection volume C adapted for collecting waste materials, particularly liquids and other flowable materials, from the wound. Thus, the housing 60 is substantially at least one of impermeable, contamination and leak-free regarding these materials with respect to the external environment E, and may be formed as an integral item, or from several parts suitably joined together, for example. The container 31 is rigid or semi rigid, though in other variations of the embodiment, the container may be non-rigid, and is suitably adapted for connection with respect to the drive unit 40.

The pump head 14 is joined to said waste container 31, such as to form an integral pump-head/container unit 18. However, the pump head 14 or parts thereof may be formed integrally with the waste container 31, or alternatively each component may be formed separately and joined together in any suitable manner, for example bonding, welding, fastening, and so on, to form the integral unit 18. At least a part of the pump head 14 is accommodated in the collection volume C, in particular, the pump inlet port 19 and pump outlet port 20 are at least partially accommodated within said collection volume C, while the diaphragm 24 is facing in a direction generally away from collection volume C. The pump head 14 is located with respect to the container 31 at a position such that when the container 31 is coupled to the drive unit 40, the diaphragm 24 is aligned with the smooth surface 55. The natural resilience of the diaphragm 24 generally results in the pump head 14 defining size of variable internal volume P intermediate between the said maximum and minimum pump volume P, if not the maximum pump volume P, when the pump head 14 is disengaged from the drive unit 40. In such a position, or even if the diaphragm 24 were to be at the first position defining a minimum pump volume P, the suction pump 25 engages the smooth surface 55 automatically, either immediately when the waste container 31 is coupled to the drive unit 40, or very soon after operation of the drive unit, when the reciprocating mechanism pushes the reciprocating head into engaging contact with the diaphragm 24.

In the first embodiment illustrated in FIG. 1, the enclosure 12 is in direct fluid communication with the pump inlet port 19 via conduit 16 that extends from the enclosure 12 and is connected to a nipple 65 on the container housing 60, and thence via a second conduit 67 that projects into the volume C from the nipple 65 and is sealingly fixed to the inlet port 19.

The outlet port 20 discharges or drains, via optional sleeve 69, fluids that are sucked into the pump head 14 from the enclosure 12 into the collection volume C of the container 31.

In this embodiment, the container 31 also comprises a vent 17 for venting the collection volume C to the external environment E. A suitable biological filter, hydrophobic filter or other filter (not shown) may be provided at vent 17 to prevent contamination of the external environment E from the contents of the container 31.

The container 31, or indeed pump-head/container unit 18, comprises an interface 62 that faces, and has a form that is generally complementary to, a drive unit interface 64 on the housing 52, for facilitating mounting or attaching the pump-head/container unit 18 (or container 31) with respect to the drive unit 40. The system further comprises a suitable coupling and locking mechanism, including suitable attachments means on each of the pump-head/container unit 18 (or container 31) and the housing 52 or drive unit 40, for allowing attachment or detachment one from the other, and the attachment means allow attaching of the container and/or pump head to the drive unit by a simple manipulation without tools. Such attachment means may comprise, for example latch 23 engageable with tooth 30, and tab 44 engageable with slot 45, which enabling coupling and decoupling of the pump-head/container unit 18 (or container 31) with respect to the drive unit 40.

In this embodiment, the pressure regulator 35 may be mounted to the enclosure 12 at any suitable position, though typically at a position where operation thereof will be unhindered by other equipment or parts of the patient's body, or where operation thereof will not be compromised by specific treatments that may be needed to be administered to the patient. Alternatively, the regulator 35 may be mounted in a suitable conduit, for example at an end of a conduit that is fixed to the enclosure 12, and such an arrangement may be useful in cases where the area directly over the enclosure is unsuitable, for example where the patient is covered with blankets which are also draped over the enclosure.

The pressure regulator 35 comprises a vent valve arrangement having a valve seal 38 that cooperates with valve seat 68 for providing sealing engagement therewith when the regulator 35 is in the closed position. The valve seal 38 is mounted on a pin 72 having a nut 59 thereon, the axial position of which relative to the pin is adjustable. The pin 72 is reciprocably movable within the lumen of a helical spring 37, located between the nut and the enclosure 12, between an open position in which the seal 38 is displaced from the seat 68, and the said closed position. The regulator 35 is urged to the open position when there is a pressure difference between the ambient air pressure of the external ambient environment E and the pressure within the confined volume V that exceeds a threshold value M. When this pressure difference is at or less than the threshold value M, the regulator 35 is urged to the closed position by means of the restoration force of the spring 37. The datum restoration force provided by spring 37 can be adjusted by means of nut 59, in order to control the threshold value M, and thus the vacuum conditions in the confined volume V at which the regulator 35 opens to the external environment E.

Optionally, the regulator 35 may also comprise a biological or other suitable filter to prevent possible contamination of the wound via the confined volume V, and/or possible contamination of the external environment E.

The integral unit 18 comprising container 31 and valve head 14 may be provided as a kit 90, which may also comprise conduit 16, enclosure 12 and regulator 35, optionally already connected to the unit 18. Alternatively the conduit 16, enclosure 12 and regulator 35, may be provided separately. The kit 90 typically also comprises a sterile bag or other packaging (not shown) that is removed before use, and after a single or one-time use it is disposed of, typically in a contamination-free manner. Thus, the unit 18 may be made from relatively inexpensive materials, compared with, for example, the manufacturing costs of the drive unit 40, and in any case may also be made from medically compatible materials, including suitable plastics and so on.

Thus, the system comprises a disposable part, including integral unit 18 conduit 16, enclosure 12 and regulator 35, and a reusable part, including the pump drive unit 40.

The system 10 according to the first embodiment may be operated as follows. Unit 18, interconnected with the conduit 16 and enclosure 12, is mounted to drive unit 40, such that the pump head 14 is engaged with the reciprocating head 54, and locked together via latch 23. The control unit 40 may be switched on temporarily for driving the reciprocating head 26 through one or half of a reciprocation cycle as necessary to ensure that the suction cup 25 is firmly engaged on the smooth surface 55. The enclosure 12 is placed over the wound site so as to cover the same, and the periphery 51 sealingly abutting the body 34, for example with the aid of bandages, dressings, adhesive tape, and so on. The nut 59 is adjusted to provide the required setting for the pressure regulator 35. The drive unit 40 is switched on, and as the motor 39 is activated, the crank turns, reciprocating the rod and reciprocating head 26, causing the diaphragm 24 to reciprocate with diaphragm 54 and thus alternately increase and decreased the pump volume P. Thus, as the pump head 14 begins to operate, air and fluids exuded from the wound are sucked out of the contained volume V, providing a negative pressure thereat and creating a partial vacuum. Fluids and other exudate materials in the wound are drawn and carried through the conduit 12 and conduit 67 directly to the inlet port 19, through the pump working chamber 29 (which is at a below-ambient, or negative, pressure when operating), and out of the outlet port 20 to the container volume C via discharge sleeve 69. If the pressure in the confined volume V drops too much, then the pressure difference threshold M is exceeded, and the seal 38 becomes unseated, allowing ingress of external ambient air into the confined volume V. The flow of air into the confined volume V vents the enclosure and aids in entraining the fluids and materials from the wound towards the pump head 14, in particular where they may be blocking part of the passage to the inlet port 19. As diaphragm 24 reciprocates, it may induce partial cyclic flow within the conduit 16 as the air pulsates, and this may cause the pressure in the enclosure 12 to fluctuate to some degree, enhancing drainage of exudates from the wound. The relatively sudden opening of the pressure regulator 35, under the appropriate pressure conditions, may also provide a pulse effect that may help to dislodge blockages etc.

If necessary, the nut 59 may be adjusted to allow operation of the regulation valve at lower or higher vacuum levels in the enclosed volume V. As exudates fills the collection volume C, air is displaced out of this volume via vent 17.

If conduit 16 becomes blocked, the vacuum created by the pump 50 is increased by the action of the pump head 14 until the blockage is dislodged and displaced to the waste container, which may have the effect of reducing the vacuum in the contained volume V, which in turn may cause the regulator to open and allow air thereinto.

If the container volume C of container 31 reaches full capacity, for example the collected materials or exudates 49 reaching the level of the outlet port 20 or any other suitable level, the unit 18, conduit 16, and enclosure 12 may be disconnected from the drive unit 40 and disposed of, in a similar manner to an end of treatment, as described below, and a new unit 18, conduit 16, and enclosure 12 used with the drive unit 40 to continue treatment. Alternatively, it is possible to remove and dispose of the unit 18, optionally including conduit 16, and to replace just these items to continue treatment. In such a case, patient discomfort is reduced, as the wound site is left alone. In other situations it may be necessary to change or replace the wound enclosure 12 while leaving the conduit 16 and/or the unit 18 in place. Thus, sometimes a kit comprising the range of items including unit 18, conduit 16, and enclosure 12 is useful, while at other times a variety of kits comprising just unit 18, or unit 18 and conduit 16, or conduit 16, or conduit 16 and enclosure 12, or enclosure 12 may also be useful.

After the completion of the wound suction treatment, the drive unit 40 is switched off, and the unit 18 is unlatched from the drive unit 40, automatically disengaging the pump head 14 from the reciprocating head 26, and the wound enclosure is removed from the patient. The unit 18, conduit 16, and enclosure 12 are then disposed of.

Figure 2:
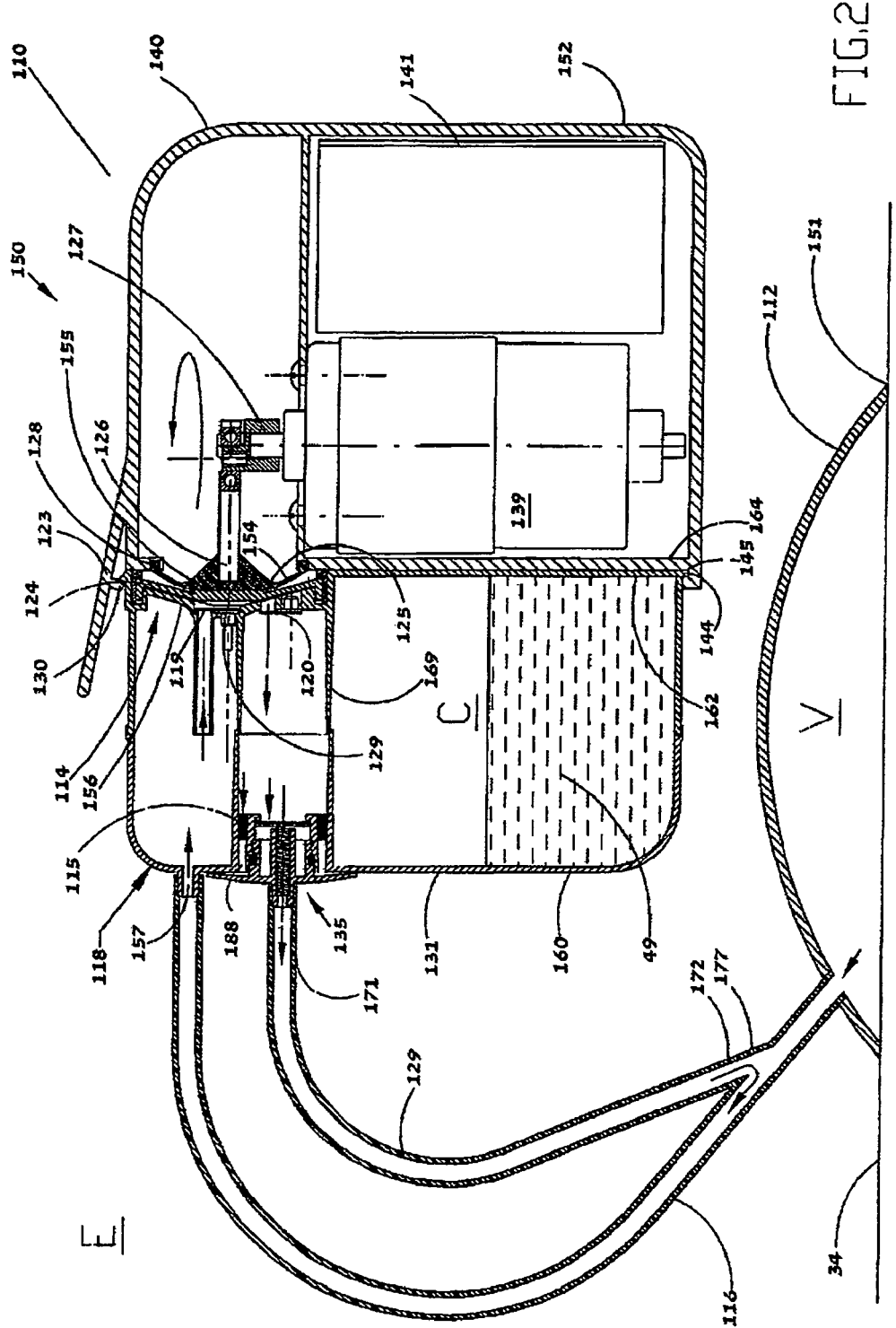
FIG. 2 is a schematic illustration in cross-sectional side view of a second embodiment of the invention, wherein the pump-head/container unit is attached to the pump drive unit, and the wound enclosure is fixed to a wound site.

A vacuum system for draining an open wound according to a second embodiment of the present invention, illustrated in FIG. 2, comprises the elements and features of the first embodiment, with some differences as described below, mutatis mutandis. Thus, the system 110 according to the second embodiment also comprises a wound enclosure 112, and a vacuum pump 150, waste canister or container 131, and pressure regulator 135.

The wound enclosure 112 is similar to that of the first embodiment, mutatis mutandis, having an outer perimeter 151 that is sealable to the periphery of the wound area on the body 34 and defining a confined volume V, with the main difference with respect to the first embodiment being that the pressure regulator 135 is not mounted to the enclosure 112, but elsewhere as will be further explained.

The vacuum pump 150 is similar to that of the first embodiment, mutatis mutandis, and thus comprises a pump head 114 that is releasably coupled to a pump drive unit 140 for operation therewith, the drive unit 140 comprising housing 152, drive unit interface 164, electric motor 139, battery pack 141, reciprocating mechanism 127 (comprising a crank, rod, reciprocating head 126 having a flexible membrane 154 comprising periphery 128, and smooth surface 155, similar to the corresponding components described for the first embodiment, mutatis mutandis. The pump head 114 comprises rigid part 156 having a pump inlet port 119 and a pump outlet port 120 with suitable one-way valves, and a flexible diaphragm 124 (having a suction cup 125), defining a pump working chamber 129 having a variable pump volume P, similar to the corresponding components described for the first embodiment, mutatis mutandis.

The waste container 131 is similar to that of the first embodiment, mutatis mutandis, and thus comprises housing 160 defining collection volume C, interface 162, coupling/decoupling and locking mechanisms, for example such as latch 123 and tooth 130, tab 144 and slot 145, similar to the corresponding components described for the first embodiment, mutatis mutandis.

In the second embodiment, the pump head 114 is also joined to said waste container 131, to form an integral unit 118 similar to the corresponding components described for the first embodiment, mutatis mutandis, and the pump inlet port 119 and pump outlet port 120 are at least partially accommodated within said collection volume C, while the diaphragm 124 is facing in a direction generally away therefrom.

In contrast with the first embodiment, in the second embodiment the enclosure 112 is in direct fluid communication, via conduit 116 and waste container inlet port defined by nipple 157, with the container 131, rather than the pump inlet port 19, which in this embodiment opens to the collection volume C. Thus, exudates from the wound are directly discharged to the collection volume C. The outlet port 120, on the other hand, discharges to sleeve 169 that extends to the outside of the housing 160 via exit port 188. The outlet port 120 is thus vented to the external ambient environment E, and thus there is no direct communication between the container volume C and the outlet port 120. The container 131 does not comprise a vent corresponding to vent 17 of the first embodiment for venting the collection volume C. In the second embodiment, the pressure regulator 135 is mounted to a first end 171 of a second conduit 123 that provides fluid communication between the pressure regulator 135 and the enclosure 112. The second end 172 of conduit 123 is spliced from conduit 116 at juncture 177, so that there is a tube conduit connected to enclosure 112, bifurcating to conduits 116 and 123. Juncture 177 is close to the enclosure 112, but alternatively may be at any other location along the length of conduit 116. Alternatively, in other variations of this embodiment, the second conduit 123 may be connected directly to the enclosure independently of the first conduit 116. Alternatively, in yet other variations of this embodiment, the second conduit 123 may be connected to the first conduit 116 along a length thereof, and optionally may comprise separate lumens of a bi-lumen conduit. Other arrangements for the conduits 123, 116 are also possible.

Figure 3:
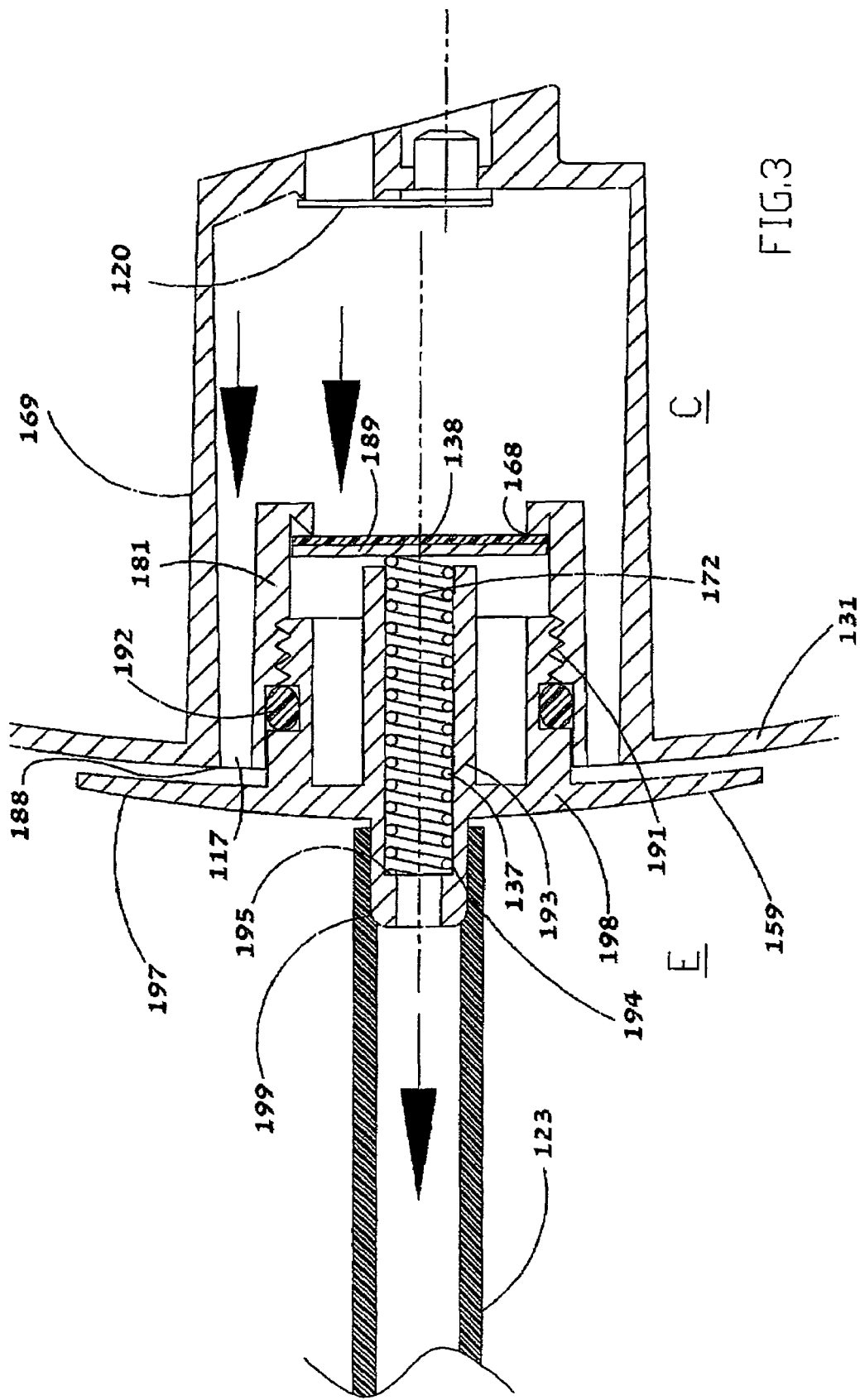
FIG. 3 is a schematic illustration in fragmented cross-sectional side view of the pressure regulator of the embodiment of FIG. 2.

As illustrated in greater detail in FIG. 3, the pressure regulator 135 is coaxially accommodated in sleeve 169, such as to allow ventilation of the space within sleeve 169 via annular gap 117 formed between.

Optionally, the vent 117 may also comprise a biological or other suitable filter 115 (shown in FIG. 2) to prevent possible contamination of the external environment E via flow from the outlet port 120.

The pressure regulator 135 according to the second embodiment comprises a vent valve arrangement having an outer annular valve body 181 coaxial with said sleeve 169 and defining said annular gap 117. The valve body inwardly projects from said exit port 188, and comprises a radial inner facing flange defining annular valve seat 168. The valve body 181 is generally static, and may be integrally formed or otherwise joined, mounted or connected in coaxial relationship with sleeve 169. An annular adjustor nut 159 comprises an outer annular body 198 that is adjustably engageable with the valve body 181 via screwthreads 191 that allow controlled relative axial displacement between the nut 159 and valve body 181. Seal 192 prevents leakage between the valve components. The nut 159 comprises an inner sleeve 193 coaxial with and radially displaced with respect to outer annular body 198 via annular plate 197. The inner sleeve 193 defines a stepped lumen 194 with annular shoulder 195 therethrough. Valve seal 138, backed by disc or plate 189, is biased by compression helical spring 137 against valve seat 168. Helical spring 137, which is seated on shoulder 195, is reciprocably movable within the lumen 194 to enable the valve seal 138 to cooperate with valve seat 168 for providing sealing engagement therewith when the regulator 135 is in the closed position, and to enable the valve seal 138 to be displaced from valve seat 168 when the regulator 135 is in the open position. The lumen 194 extends via nipple 199 in a direction towards the outside of the container 131 and allows connection of said end 171 of conduit 123 thereto.

In a similar manner to the first embodiment, mutatis mutandis, the regulator 135 is urged to the open position when there is a pressure difference between the ambient air pressure of the external ambient environment E and the pressure within the confined volume V that exceeds a threshold value M. As the sleeve 169 is vented to the external ambient environment E, via vent 117, the ambient pressure of the external ambient environment E is maintained in sleeve 169, and thus with respect to the seal 138 and outlet port 120. When this pressure difference is at, or less than, the threshold value M, the regulator 135 is urged to the closed position by means of the restoration force of the spring 137.

The datum restoration force provided by spring 137 can be adjusted by means of a compression control mechanism in the form of nut 159, in order to control the compression of the spring, and the magnitude of threshold value M, and thus the vacuum conditions in the confined volume V at which the regulator 135 opens to the external environment E. As the nut 159 is rotated clockwise or anticlockwise, the relative axial relationship between the shoulder 195 and valve seat 168 is varied in one or another direction, thereby adjusting the potential energy of the pre-stressed spring 137 and thus the magnitude of the pressure-induced force acting on the valve seal 138 that is necessary to unseat and open the pressure regulator 135.

As with the first embodiment, mutatis mutandis, the integral unit 118 may be provided as a kit 90, which may also optionally comprise one or more of conduits 116 and 123, regulator 135 and enclosure 112, optionally already connected to the unit 118, or alternatively, one or more of conduits 116 and 123, regulator 135 and enclosure 112, may be provided separately to the integral unit 118.

The system 110 according to the second embodiment may be operated in a similar manner to the first embodiment. Unit 118, interconnected with the conduits 116, 123 and enclosure 112, is mounted to drive unit 140, and the enclosure 112 is placed over the wound site in a similar manner to that with the first embodiment, mutatis mutandis. The nut 159 is adjusted to provide the required setting for the pressure regulator 135, and the drive unit 140 is switched on. As the pump head 14 begins to operate, air and fluids exuded from the wound are sucked out of the contained volume V, and are drawn and carried through the conduit 112, most of the liquid exudates discharging directly to the collection volume C of the container 131. However air is drawn into the inlet port 119, through the pump working chamber 129 (which is at a below-ambient, or negative, pressure when operating), and out of the outlet port 20 to the sleeve 169, and subsequently vented. If the pressure in the confined volume V drops such that the pressure difference threshold M is exceeded, and the seal 138 becomes unseated, allowing ingress of external ambient air and/or the air discharged from the outlet port 120 into the conduit 123 via sleeve 169. This ingressed air then recirculates to the collection volume C via conduit 116, and this flow recirculation also entrains air and flowable material from the wound enclosure 112. If, in other variations of the second embodiment, the conduit 123 is attached directly to the wound enclosure 112, independently of conduit 116, then the recirculating flow also directly includes the confined volume V as well. In any case, the recirculating flow of air helps to vents the enclosure 112 and aids in entraining the fluids and materials from the wound towards the pump head 114. This recirculation also helps to reduce the amount of contaminated air that may be discharged to the external environment. As with the first embodiment, mutatis mutandis, the nut 159 may be adjusted to allow operation of the regulation valve at lower or higher vacuum levels in the enclosed volume V. On the other hand, the relatively large collection volume C disposed between the wound enclosure 112 and the pump inlet port 119 tends to dampen the pulsating effect generated by the reciprocating operation of the pump head 114.

Disconnection of the unit 118, with or without the conduits 112, 123, pressure regulator 135, and enclosure 112 is similar to that described for the first embodiment, mutatis mutandis, and the used components are then disposed of.

In the method claims that follow, alphanumeric characters and Roman numerals used to designate claim steps are provided for convenience only and do not imply any particular order of performing the steps.

It should be noted that the word "comprising" as used throughout the appended claims is to be interpreted to mean "including but not limited to".

While there has been shown and disclosed example embodiments in accordance with the invention, it will be appreciated that many changes may be made therein without departing from the spirit of the invention.

The invention claimed is:

1. A vacuum system for providing a sub-ambient pressure to a medical target volume, comprising:
   a suction head having an inlet arrangement adapted for being in fluid communication with said target volume;
   a vacuum pump in fluid communication with said suction head, said vacuum pump being adapted for providing a working pressure in said system below external ambient pressure, said vacuum pump comprising a pump head releasably operatively connected to a pump drive unit, wherein said pump head comprises a pump inlet port, a pump outlet port and a suitable deformable diaphragm arrangement reciprocable by means of said pump drive unit to induce said working pressure in said vacuum system;

a waste container defining a collection volume for enabling collection of drained materials from said target volume, wherein said pump head is one of fixed to or integral with said waste container such that said pump inlet port and said pump outlet port are accommodated in said collection volume, wherein said pump inlet port is in fluid communication with said suction head via a conduit connecting said pump inlet port with said suction head, at least a portion of said conduit being accommodated in said collection volume, wherein said pump outlet port discharges into said collection volume, and wherein said waste container is vented to external ambient air; and a venting valve arrangement mounted to one of said conduit and suction head adapted for enabling ingress of external ambient air into the system responsive to a reduction in said working pressure below a predetermined datum pressure with respect to said external ambient pressure, such as to induce suction flow of materials from said target volume when in use, and for discontinuing said ingress when said datum pressure is restored.

2. A vacuum system according to claim 1, wherein said venting valve arrangement comprises an inlet port having a valve seat and in fluid communication with said ambient air, an outlet port in fluid communication with said vacuum system, and a valve seal biased for sealingly closing with respect to said valve seat by means of a resilient element generating a biasing force of magnitude substantially less than and in a direction generally opposed to a pressure-induced force acting on said valve seal when said working pressure is less than said datum pressure.

3. A vacuum system according to claim 1, wherein said venting valve arrangement comprises an adjustment mechanism for adjusting said datum pressure.

4. A vacuum system according to claim 3, wherein said venting valve arrangement comprises an inlet port in fluid communication with said ambient air and an outlet port in fluid communication with said vacuum system, and a valve seal biased for sealingly closing said inlet port by means of a resilient element generating a biasing force of magnitude substantially less than and in a direction generally opposed to a pressure-induced force acting on said valve seal when said working pressure is less than said datum pressure, and wherein said adjustment mechanism comprises a bias adjusting arrangement for adjusting the magnitude of said biasing force.

5. A vacuum system according to claim 4, wherein said resilient element comprises a compression spring mounted in a suitable housing such as to urge said valve seal towards said valve seat, and said bias adjusting arrangement comprises a compression control mechanism for adjusting the compression of said spring.

6. A vacuum system according to claim 1, wherein said venting valve arrangement is connected to said suction head via a suitable conduit.

7. A vacuum system according to claim 1, wherein said drive unit comprises a reciprocation drive for driving a reciprocating member, and said diaphragm is releasably engageble with said reciprocating member responsive said pump head being coupled to said pump unit.

8. A vacuum system according to claim 7, wherein said reciprocating member and said diaphragm are conformally shaped such that when coupled one with the other a vacuum is created therebetween.

9. A vacuum system according to claim 1, wherein a part of said pump head is accommodated in said waste container, wherein said diaphragm is facing a direction generally away from said collection volume, and wherein said pump inlet port and a pump outlet port are at least partially within said collection volume.

10. A vacuum system according to claim 1, wherein said pump head, waste container and suction head are configured for being disposable.

11. A vacuum system according to claim 1, wherein said target volume is associated with a wound, burn or the like, and said suction head comprises an enclosure sealable to a perimeter of the wound so as to define a confined volume comprising said target volume.

12. A vacuum system according to claim 1, wherein said suction head comprises a drain catheter having at least one lumen in fluid communication with said pump, and said inlet arrangement comprises at least one aperture adapted for providing fluid communication between said target volume and said at least one lumen.

13. A vacuum system according to claim 1, wherein said pump head and waste container are reversibly lockably engaged with said pump drive unit by means of a latch arrangement.

14. A vacuum system for providing a sub-ambient pressure to a medical target volume, comprising:

a suction head having an inlet arrangement adapted for being in fluid communication with said target volume;

a vacuum pump in fluid communication with said suction head, said vacuum pump being adapted for providing a working pressure in said system below external ambient pressure, said vacuum pump comprising a pump head releasably operatively connected to a pump drive unit, wherein said pump head comprises a pump inlet port, a pump outlet port and a suitable deformable diaphragm arrangement reciprocable by means of said pump drive unit to induce said working pressure in said vacuum system;

a waste container defining a collection volume for enabling collection of drained materials from said target volume, wherein said pump head is one of fixed to or integral with said waste container such that said pump inlet port and said pump outlet port are accommodated in said collection volume, wherein said pump inlet port is in fluid communication with said suction head via said collection volume, and said waste container is in fluid communication with said suction head via a first conduit, and wherein said pump outlet port is vented to external ambient air; and a venting valve arrangement in fluid communication with said suction head via a second conduit, said valve arrangement being mounted to said waste container and in selective fluid communication with said pump outlet port for enabling ingress of at least one of fluid from said vacuum pump outlet port and external ambient air into the system responsive to a reduction in said working pressure below a predetermined datum pressure with respect to said external ambient pressure, such as to induce suction flow of materials from said target volume when in use, and for discontinuing said ingress when said datum pressure is restored.

15. A vacuum system according to claim 14, wherein said first conduit and said second conduit are in fluid communication one with another.

16. A vacuum system according to claim 14, wherein said pump head and waste container are reversibly lockably engaged with said pump drive unit by means of a latch arrangement.

17. A vacuum system according to claim 14, wherein said venting valve arrangement comprises an inlet port having a valve seat and in fluid communication with said ambient air, an outlet port in fluid communication with said vacuum system, and a valve seal biased for sealingly closing with respect to said valve seat by means of a resilient element generating a biasing force of magnitude substantially less than and in a direction generally opposed to a pressure-induced force acting on said valve seal when said working pressure is less than said datum pressure.

18. A vacuum system according to claim 14, wherein said venting valve arrangement comprises an adjustment mechanism for adjusting said datum pressure.

19. A vacuum system according to claim 18, wherein said venting valve arrangement comprises an inlet port in fluid communicaton with said ambient air and an outlet port in fluid communication with said vacuum system, and a valve seal biased for sealingly closing said inlet port by means of a resilient elelment generating a biasing force of magnitude substantially less that an in a direction generally opposed to a pressure-induced force acting on said valve seal when said working pressure is less than said datum pressure, and wherein said adjustment mechanism comprises a bias adjusting arrangement for adjusting the magnitude of said biasing force.

20. A vacuum system according to claim 19, wherein said resilient element comprises a compression spring mounted in a suitable housing such as to urge said valve seal towards said valve seat, and said bias adjusting arrangement comprises a compression control mechanism for adjusting the compression of said spring.

21. A vacuum system according to claim 14, wherein said drive unit comprises a reciprocation drive for driving a reciprocating member, and said diaphragm is releasably engageble with said reciprocating member responsive said pump head being coupled to said pump unit.

22. A vacuum system according to claim 21, wherein said reciprocating member and said diaphragm are conformally shaped such that when coupled one with the other a vacuum is created therebetween.

23. A vacuum system according to claim 14, wherein a part of said pump head is accommodated in said waste container, wherein said diaphragm is facing a direction generally away from said collection volume, and wherein said pump inlet port and a pump outlet port are at least partially within said collection volume.

24. A vacuum system according to claim 14, wherein said pump head, waste container and suction head are configured for being disposable.

25. A vacuum system according to claim 14, wherein said target volume is associated with a wound, burn or the like, and said suction head comprises an enclosure sealable to a perimeter of the wound so as to define a confined volume comprising said target volume.

26. A vacuum system according to claim 14, wherein said suction head comprises a drain catheter having at least one lumen in fluid communication with said pump, and said inlet arrangement comprises at least one aperture adapted for providing communication between said target bolume and said at least one lumen.

* * * * *

UNITED STATES PATENT AND TRADEMARK OFFICE
CERTIFICATE OF CORRECTION

| | | |
|---|---|---|
| PATENT NO. | : 7,503,910 B2 | |
| APPLICATION NO. | : 11/344007 | |
| DATED | : March 17, 2009 | |
| INVENTOR(S) | : Carmeli Adahan | |

It is certified that error appears in the above-identified patent and that said Letters Patent is hereby corrected as shown below:

Title page, Item (56) References Cited:

Please add the following U.S. patent documents cited in the August 21, 2007 Office Action:

| | | |
|---|---|---|
| US 6,824,533 B2 * | 11/2004 | Risk, Jr. et al. |
| US 1,599,899 * | 09/1926 | Kettering et al. |
| US 4,611,627 * | 09/1986 | Eidsvoog et al. |
| US 4,447,226 * | 05/1984 | Mayoral |
| US 6,562,013 B1 * | 05/2003 | Marasco, Jr. |

Claim 19, Column 19, Lines 23 – 27:

Please delete "... in fluid communicaton ... resilient elelment generating ... less that an in ..."

and replace with

-- in fluid communication ... resilient element generating ... less than and in --

UNITED STATES PATENT AND TRADEMARK OFFICE
CERTIFICATE OF CORRECTION

PATENT NO.       : 7,503,910 B2
APPLICATION NO.  : 11/344007
DATED            : March 17, 2009
INVENTOR(S)      : Carmeli Adahan It is certified that error appears in the above-identified patent and that said Letters Patent is hereby corrected as shown below:

Claim 26, Column 20, Lines 31 – 32:

Please delete "... providing communication ... target bolume and ..."

and replace with

-- providing fluid communication ... target volume and --

Signed and Sealed this

Twenty-fifth Day of August, 2009

David J. Kappos
*Director of the United States Patent and Trademark Office*